United States Patent [19]

Beaver

[11] 4,005,382

[45] Jan. 25, 1977

[54] SIGNAL PROCESSOR FOR ULTRASONIC IMAGING

[75] Inventor: William L. Beaver, Los Altos Hills, Calif.

[73] Assignee: Varian Associates, Palo Alto, Calif.

[22] Filed: Aug. 7, 1975

[21] Appl. No.: 602,700

[52] U.S. Cl. .............................. 340/1 R; 340/6 R; 343/100 SA

[51] Int. Cl.² ...................... G01S 9/66; G01S 3/80

[58] Field of Search ............. 343/100 SA; 340/1 R, 340/6 R; 73/67.8 S

[56] References Cited

UNITED STATES PATENTS 3,936,791  2/1976  Kossoff ............................. 340/1 R Primary Examiner—Richard A. Farley
Attorney, Agent, or Firm—Stanley Z. Cole; Gerald M. Fisher; John J. Morrissey

[57] ABSTRACT

A signal processor for an ultrasonic imaging system permits the selection of scan angles and focusing distances. The system includes an ultrasonic receiver comprising an array of electromechanical transducers, with the individual transducers being coupled to phase selection circuitry whereby non-continuous delay values can be introduced between adjacent transducers. Proper selection of the delay values between adjacent transducers can accomplish preferential ultrasonic reception or transmission in particular directions. An optimized switching arrangement minimizes the number of electronic components required to provide the desired delay values.

7 Claims, 5 Drawing Figures

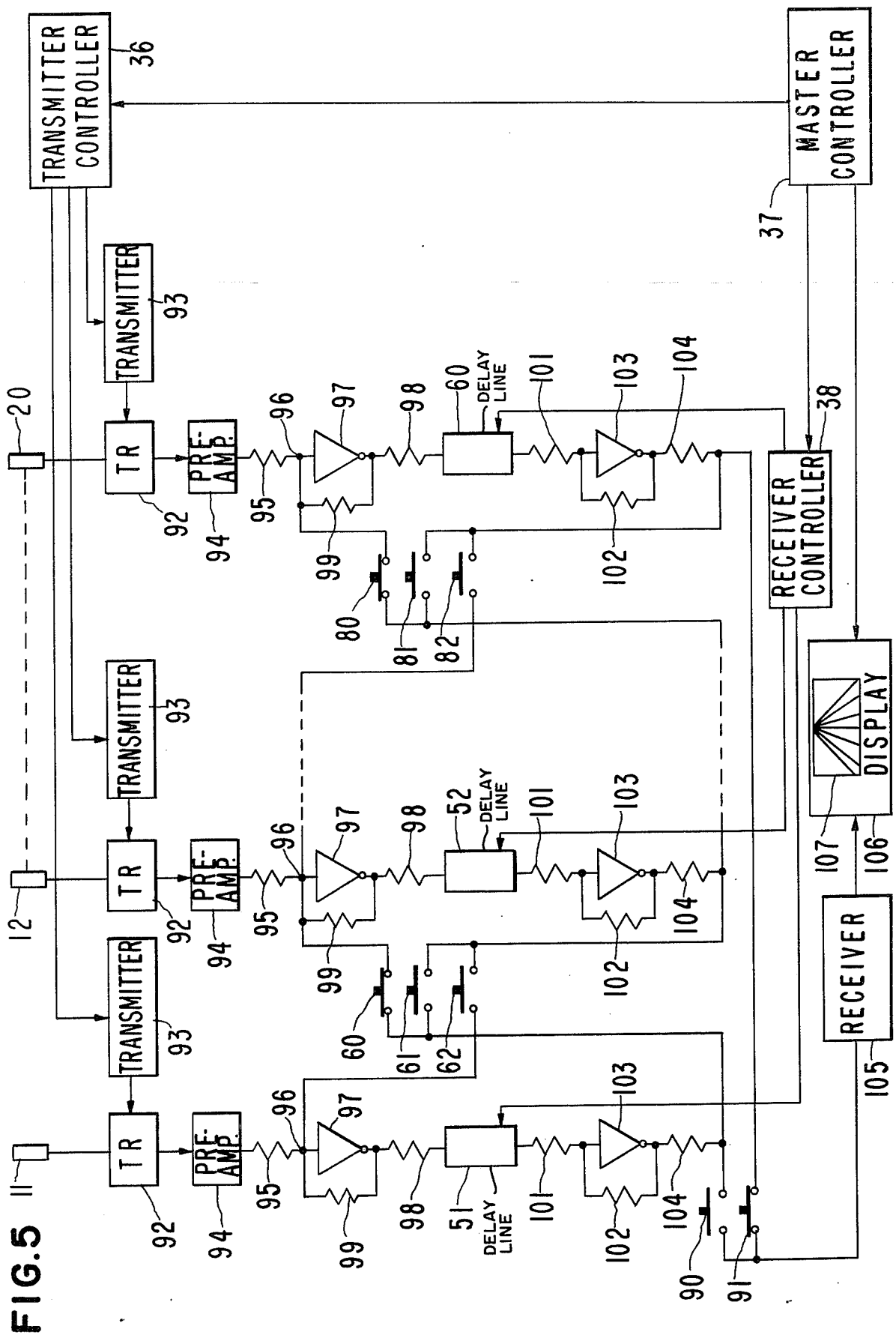

SIGNAL PROCESSOR FOR ULTRASONIC IMAGING

BACKGROUND OF THE INVENTION

1. Field of the Invention:

This invention is a further development in the field of direction selecting for ultrasonic imaging systems. In particular, the invention is concerned with the introduction of discontinuous delay values between the various elements of an array of transducers, and with an optimized switching arrangement for minimizing the number of electronic components required to provide the required delay values for steering and focusing of the ultrasonic imaging system.

2. Description of the Prior Art:

In a pulsed ultrasonic beam imaging apparatus, a particular scanning angle and focal distance for an array of electromechanical transducers can be obtained by pulsing each of the transducer elements of the array in a proper timing sequence, so that the acoustic pulses transmitted from each of the transducer elements all arrive at the desired focal point at the same instant in time. This principle is illustrated schematically in FIG. 1 where the transducer array 10 consists of an unspecified number of individual transducer elements, with the element on the left end being indicated by the reference number 11, the element on the right end being indicated by the reference number 20, and intermediate elements of the array being indicated by the reference numbers 12, . . . , 15, . . . , 19. The element 15 represents the transducer element disposed at or near the center of the array. In order to focus an acoustic pulse at the point P which is located at a distance from the transducer array 10, it is necessary that the pulses transmitted from the individual transducers all arrive at point P at the same time. Thus, the acoustic pulse from the left-end transducer 11 must travel to a point B on the pulse path to the focal point P before the right-end transducer element 20 is excited to emit an acoustic pulse. By delaying the electrical excitation of each of the transducer elements to the right of the end element 11 by an appropriate amount, it is possible to bring the pulses from all the transducer elements simultaneously to a focus at point P. The focal point P is identified by the focal distance f from the center element 15 to the point P, and by the angle A between the normal to the array at the center element 15 and the path from center element 15 to point P.

Similarly, in order to operate the transducer array 10 in a receiving mode so as to focus upon the point P as a source of reflected acoustic energy, it is necessary that, as a wave front reflected from the point P impinges in turn upon each of the transducer elements of the array, the electronic signals thereby generated by each of the transducer elements in succession be detected simultaneously by a receiver. For example, as seen in FIG. 1, a signal reflected from the point P will arrive simultaneously at the right-end transducer element 20 and at the point B on the path from point P to the left-end transducer element 11. Therefore, the electronic signal produced by the right-end transducer element 20 when operating in the receiving mode must be delayed during the time interval required for the acoustic wave front travelling along the path from point P to the left-end transducer element 11 to travel the distance from point B to element 11. The electronic signals generated by the intermediately disposed transducer elements of the array 10 must likewise be delayed by suitable intermediate time intervals before being combined so as to provide a coherent image of the point P.

Various techniques have been used in prior art imaging systems for obtaining coherent delays between the individual receiving elements of a transducer array in order to provide an electronic analog image of the source of reflected waves. One such prior art technique is shown in FIG. 2 where the transducer elements 11, 12, . . . , 20, representing an unspecified number of transducer elements, are arranged in a linear array with the left-end element being indicated by reference number 11 and the right-end element being indicated by the reference number 20. Each transducer element is coupled through a separate variable delay line 21, 22, . . . , 30, respectively, to a transmit/receive unit 31. The transmit/receive unit 31 is programmed to transmit electrical pulses to the individual transducer elements for conversion into acoustic pulses, and to receive electrical pulses generated in the individual transducer elements by reflected ultrasonic waves. The processing of the received signals by the the transmit/receive unit 31 occurs during the quiescent period between pulse transmissions. The particular delay value for each of the variable delay elements 21, 22, . . . , 30 is controlled by a controller 35, and is determined by the desired scanning angle for the array.

Typically, the individual transducer elements of the array 10 are spaced apart by one-half wavelength. This requirement is dictated by the desire for good resolution in the optical sense for the source of reflected waves being imaged. The variable delay lines could provide either continuously variable delay values or could be digitally switched between various discrete delay values. The electronic circuitry required for providing continuously variable delay values is more complicated than circuitry for providing digital switching between discrete delay values, and consequently for most practical applications switching circuitry is provided to enable digital switching between various delay values. max For digitally switched delay lines, the criterion for good image formation is that the phase error produced at any given transducer element be less than $\pm \lambda/8$ where $\lambda$ is the acoustic wavelength of the ultrasonic wave in the medium through which it is travelling. To satisfy this criterion, the number of delay values (or steps) $n$ into which the dynamic range of a given delay element can be divided should be greater than $2 N \sin \theta_{max}$, where N is the total number of transducer elements in the array and $\theta_{max}$ is the maximum steering angle or scanning angle measured from the normal to the array. In deriving this relationship, the focal length $f$ of the array is assumed to be large compared to the dimensions of the array, and the centers of adjacent array elements wave assumed to be separated by $\lambda/2$. For a typical array comprising 32 transducer elements and a maximum steering angle of 45°, this criterion for good image resolution requires that there be 46 or more delay steps for each of the delay lines.

Another arrangement known to the prior art for obtaining coherent delays between the transducer elements of an ultrasonic imaging system is shown in FIG. 3, where the transducer elements 11, 12, 13, . . . , 20 are numbered as in FIG. 2. The left-end transducer element 11 is coupled to a fixed delay line 21, the right-end transducer element 20 is coupled to a fixed delay line 30, and the intervening transducer elements of the array are coupled to separate fixed delay lines 22, 23, . . . , respectively. The output signals from adjacent fixed delay lines are coupled, respectively, on either side of a variable delay element. For example, output signals from fixed delay lines 21 and 22 are coupled respectively to the two sides of delay element 40. The fixed delay lines 21, 22 and 23, . . . , 30 have differing values, as represented by the differing lengths thereof shown in FIG. 3. when it is intended to scan at an angle to the right of the normal to the array, the delay of the variable delay lines 40, 41 . . . 48 is greater than the difference of delay of adjacent fixed delay lines so that signals to and from transducer 20 are delayed more than the signals from other transducers to its left. The variable delay elements 40, 41, . . . , 48 are controlled by the controller 35. The electronic signal, which is generated by the right-end transducer element 20 when an ultrasonic wave front travelling from the right impinges thereon at an angle $\theta$ with respect to the normal, passes through the fixed delay line 30 to the variable delay element 48. As the wave front continues to travel after impinging the right-end transducer element 20, it impinges in succession upon each transducer element to the left of the right-end element 20. The signal generated by transducer element 19 passes through the fixed delay 29 associated therewith to the circuit line 39 where it is combined with the output of the variable delay element 48. The total delay of the signal from transducer element 20 produced by the fixed delay line 30 and variable delay element 48 is sufficiently great to allow it to combine in phase with the signal from transducer element 19 after it has passed through fixed delay line 29. The combined signals from transducers 19 and 20 are further delayed by additional variable delay elements, and combined with signals from intervening transducers. Finally, the signal contributed by the left-end transducer element 11 is coupled to the circuit line 49 at a point to the left of the variable delay element 40, and combined with the signals contributed by the preceding transducer elements.

For distantly focused ultrasonic beams, i.e., where the focal length of the array is large in comparison with the dimensions of the array, the difference in transmission time or reception time for two adjacent transducer elements is given by the expression $Y = (d/c) \sin \theta$, where $d$ is the spacing between adjacent transducer elements, $c$ is the velocity of the ultrasonic wave in the medium through which it travels, and $\theta$ is the steering angle. The maximum difference in delay time between adjacent transducer elements is $Y_{max} = (d/c) \sin \theta_{max}$. If the minimum value of delay for the variable delay elements is sufficiently small to be negligible, the difference in delays for adjacent fixed delay elements can be set to $Y_{max}$. The maximum required delay of the variable delay elements is then $2Y_{max}$. The prior art required continuously variable delay elements which were set to exact delay values to match the incident wave front. The present inventor recognizes that it is possible to achieve a minimum number of delay steps for each variable delay element in order to satisfy the phase criterion stated above. Thus for the case where the minimum value of delay for the variable delay elements 40, 41, . . . , 48 is small enough to be negligible, the number of delay steps $n$ for each variable delay element required in order to achieve good image resolution according to the criterion stated above is $n = 4 \sin \theta_{max}$. In deriving this expression, it is assumed that the spacing between adjacent transducer elements is $\lambda/2$.

The number of delay values required for each variable delay elements 40, 41 . . . 48, of FIG. 3 is reduced by a factor of N/2 compared to the number of delay values for each variable delay element 21, 22, . . . 30 of FIG. 2. However, the system of FIG. 3 required the addition of fixed delay elements 21, 22, 23, . . . 30. The delay required for the longest of these is at least $N Y_{max}$ where N is the number of transducer elements in the array. The cost and quality of delay lines is determined by the delay-band-width product. The large number of fixed delay lines and variable delay elements required by the prior art systems illustrated by FIGS. 2 and 3 and the requirement for large delay-bandwidth products for these fixed delay lines and some of the variable delay elements contribute substantially to the system cost and complexity. The present invention provides a substantial improvement over these prior art systems by permitting a substantial reduction in the number of delay values required for each variable delay element by eliminating the need for delay values with the larger delay-bandwidth products, and not requiring any fixed delay lines.

SUMMARY OF THE INVENTION

This invention provides for an ultrasonic imaging system having an array of electromechanical transducers, which can preferentially receive or transmit ultrasonic signals in the desired scanning directions. A system according to this invention has a variable delay element electrically connected to each transducer element of the array, a controller for selecting an appropriate amount of delay of each variable delay element, and switching means for selectively providing various possible electrical connection paths between adjacent delay elements so as to enable the transducer array to preferentially receive or transmit ultrasonic signals propagating either normally to the array or inclined either to the left or to the right with respect to the normal.

It is an object of this invention to enable an ultrasonic imaging system having a variable delay element coupled to each transducer element of a scanning transducer array to utilize variable delay elements having a smaller number of delay values per delay element than is required by the prior art.

It is also an object of this invention to enable an ultrasonic imaging system to scan at desired angles on either side of the normal to a scanning transducer array, without requiring that any transducer element of the array be coupled to a fixed delay element.

It is therefore an object of this invention to reduce the cost and electronic complexity of ultrasonic imaging systems by reducing the number of delay elements and the number of delay values per delay element from that required by ultrasonic imaging system known to the prior art.

It is also an object of this invention to use delay elements with smaller delay-bandwidth products than known to the prior art.

It is likewise an object of this invention to use a number of discrete delay values or steps in each variable delay line, rather than a continuous variation in delay, in an ultrasonic imaging system.

BRIEF DESCRIPTION OF THE DRAWINGS

FIG. 5 illustrates in block-diagram form a ultrasonic imaging system according to the present invention.

DESCRIPTION OF THE PREFERRED EMBODIMENT

Figure 4:
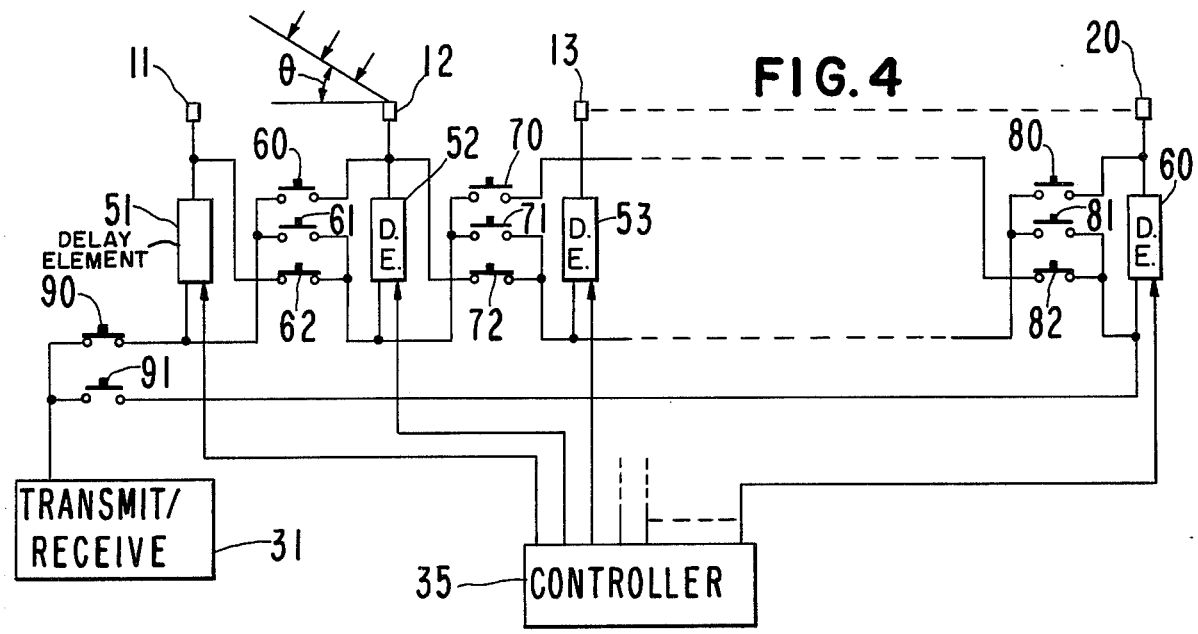
FIG. 4 illustrates in block-diagram form an ultrasonic apparatus according to the present invention.

The present invention is illustrated in block diagram form in FIG. 4. The transducer elements 11, 12, 13, . . ., 20 are shown in a linear array, although it is recognized that there are advantages in two-dimensional arrays especially in producing c-scan images. Each transducer element is coupled to a variable delay element. Thus, the left-hand transducer element 11 is coupled to a variable delay element 51, the right-end transducer element 20 is coupled to a delay element 60, and the intermediately disposed transducer elements 12, 13 . . . of the array are similarly coupled to variable delay elements 52, 53, . . . , respectively. An identical switching arrangement is provided between each adjacent pair of variable delay elements to control the delay paths of the signals generated in each of the transducer elements when operating in the transmit or receive mode. As illustrated, the switching arrangement between the variable delay elements 51 and 52 consists of three single-pole, single-throw switches 60, 61 and 62. The positions of the switches can be controlled either manually or by means of the controller 35. It is commonly understood that these switches may be transistors.

The system shown in FIG. 4 can be operating in either the transmit or receive mode. For the purposes of illustration, the operating of the system will be described in terms of receiving an ultrasonic wave front. The delay arrangements for transmission are identical to those for reception except the direction of travel of the electrical and acoustical signals are reversed. The system will also be described in terms of receiving a parallel wave front, i.e. a focus at infinity. This is done only to simplify the explanation and is not a limitation upon the system. For a wave front incident upon the transducer array from the right at an angle with respect to the normal, the right-end transducer element 20 is excited first and the left-end transducer element 11 is excited last as the incident acoustic wave front progresses. Thus, each of the transducer elements in turn from right to left generates an electronic signal in response to the incident wave front. With switch 82 closed and switches 80 and 81 open the signal from the right-end transducer element 20 will pass through the delay element 60 to components of the circuitry indicated to the left thereof in the block diagram of FIG. 4 for summation with signals generated in time-wise succession by the transducer elements to the left thereof.

To consider just two delay elements of the system in response to an ultrasonic wave impinging upon the transducer array from the right, output of the next-to-last delay element 52 can be connected through closed switch 62 to the input of the last delay element 51. The delay element 51 in addition receives an input signal from the last transducer element 11. The output of the delay element 51 is then coupled to the transmit/receive unit 31 through closed switch 90. The signal generated by the transducer element 12 must necessarily be delayed by the delay element 52 for a suitable time so as to add in phase with the signal generated by the next succeeding transducer element 11. The signals generated by the transducer elements 12 and 11 are then added coherently and are propagated through the delay element 51, and thence through the closed switch 90, to the transmit/receive unit 31 operating in the receive mode.

Signals generated by any two adjacent transducer elements can be added together in phase and then propagated as in input to a delay element which is coupled to the next succeeding transducer element, just as in the manner described above in connection with the particular adjacent transducer elements 12 and 11. Thus, in FIG. 4, the signals generated by the two adjacent transducer elements 13 and 12 can be added together in phase by connecting the output of delay element 53 through closed switch 72 to the input of delay element 52, such that the output of delay element 52 represents the summation of the output from delay element 53 together with the input signal from transducer element 12. The requirement that the output from transducer element 13 can be added to the output signal from transducer element 12 in phase can be met by the selection of an appropriate delay value for the delay element 53. As described above, the delay valve of delay element 52 is selected to provide the proper phasing with the signals from transducer element 11. In like manner, the output of any given element 52, 53, . . . , or 60, as shown in FIG. 4, can be connected to the input to the delay element in the delay path of the signal generated by the next succeeding transducer element in the general direction of propagation of the acoustic wave front.

If it is desired to scan or sweep to the left, a reflected wave front arriving from the left would strike the left-end transducer element 11 before reaching the adjacent transducer element 12. In order to detect such acoustic signals from the left, switch 60 is closed and switches 61 and 62 are open. In this arrangement, the signal generated by transducer element 11 is delayed by the delay element 51, and is then added through closed switch 60 to the signal generated by transducer element 12. The combined output from transducer elements 11 and 12 is then delayed for a suitable time by delay element 52, and is subsequently added through closed switch 70 (switches 71 and 72 being open) to the signal generated by the transducer element 13. As the acoustic wave front impinges in succession upon the other transducer elements located further to the right, the signal generated by each . successive transducer element is similarly added to the sum of the signals having passed through the delay elements associated with the preceeding transducer elements. Thus, for a wave front impinging upon the transducer array from the left, where the last transducer to be excited is the right-end transducer element 20, the signal generated by the transducer element 20 is added to the integrated output signal from the transducers 11, 12, 13, . . . , and the total integrated signal is passed as input to delay element 60. The output of delay element 60 is passed to the transmit/receive unit 31 operating in the receive mode, upon the closure of switch 91 (switch 90 being open).

In the above switching arrangement all switches 60, 70, . . . , 80 are closed for steering to the left, and all switches 62, 72, . . . , 82 are closed for steering to the right of the normal. Steering to particular angles is accomplished by switching the internal delay lines in the delay elements to different delay values. It is noted, however, that a minimum possible steering angle is determined for the above arrangement because of the irreducible minimum delay inherent in each delay element. Therefore, for steering angles smaller than the minimum angle possible with the above arrangement, including steering normal to the transducer array, an alternative switching arrangement is required.

In order to provide a selective response to an acoustic wave front incident normally upon the transducer array, the central switches 61, 71, . . . , 81 are closed, and the switches 60, 70, . . . , 80 and 62, 72, . . . , 82 are opened. The signal from each transducer element 11, 12, 13, . . . , 20 thereby passes through the delay element 51, 52, 53, . . . , 60 connected directly therewith, so that the output of all the delay elements can be summed and passed directly to the transmit/receive unit 31. By choosing equal delay values for all the delay elements 51, 52, 53, . . . , 60, the electrical signals generated by an acoustic wave front normally upon the transducer array can all be added together in phase and passed to the transmit/receive unit 31.

For steering angles close to or in the direction of the normal, the switching arrangement referred to above in which all of the switches 61, 71, . . . , 81 are closed may be modified so as to provide phase delay appropriate to the selected small angle. The modification consists of opening one or more of the switches 61, 71, . . . , 71 and closing a corresponding set of switches 60, 70, . . . , 80 for steering to the left of the normal, or closing one or more of the switches 62, 72, . . . , 82 for steering to the right, so that delay elements are connected so as to introduce delay of all signals coming from the left, or from the right, as the case may be, thereby approximating the phase delay required for the selected small steering angle.

In normal operation, only one of the three switches in each switching arrangement between adjacent delay elements is closed. Thus for the switching arrangement between delay elements 51 and 52, only one of the switches 60, 61 and 62 is normally closed. One of the switches 90 or 91 will be closed depending upon whether it is desired to steer to the right or to the left. Both switches 90 and 91 may be closed when steering straight ahead or when focusing is used. In the preferred embodiment, the transducer elements 11, 12, 13 . . . , 20 can operate in either a transmit mode or a receive mode, with receive mode operation occurring during the quiescent period between transmission pulses. It is to be understood that electronic transmission signals pass through the delay elements in the direction opposite to that of the reception signals for any given scanning angle.

The maximum delay value required for any delay element 51, 52, 53, . . . , 60 is given by the expression $Y_{max} = (d/c) \sin Y$ max. Assuming that $d = \lambda/2$, and assuming that the phase error of any element of the array is less than $\pm \lambda/8$, the number of delay steps $n$ (i.e., the maximum delay value) is given by the expression $n = 2 \sin \theta_{max}$.

Figure 3:
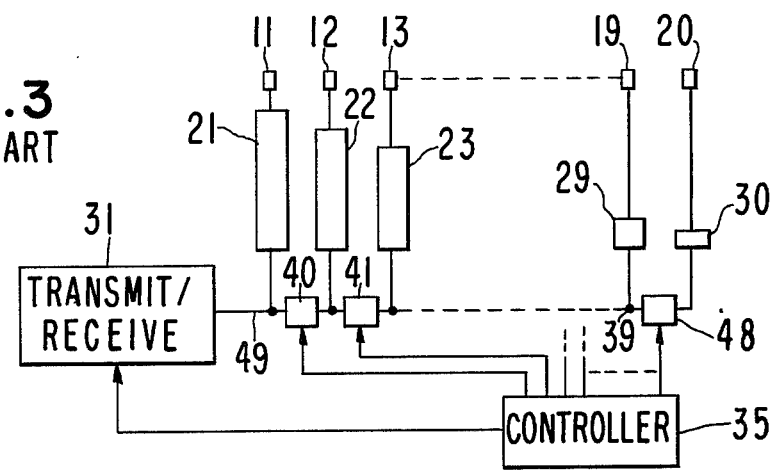
FIG. 3 illustrates in block-diagram form another particular ultrasonic imaging apparatus known to the prior art.

It is therefore apparent that an imaging system according to the present invention requires a smaller number of delay values, by a factor of 2, for each variable delay element than the prior art imaging system shown in FIG. 3.

It is also apparent that the imaging system of the present invention does not require fixed delay lines, as were required by the prior art imaging system shown in FIG. 3. Furthermore, the present invention does not require the very long total delay values that were required by the system shown in FIG. 2. This reduction in the number of delay elements and in the number of delay values per delay element provided by the present invention results in a substantial reduction in the cost and electronic complexity of an ultrasonic imaging system.

In making the comparisons above, of the various systems, it has been consistently assumed that a phase error of $\pm \lambda/8$ would be acceptable. Table I indicates the number of delay steps required for each variable delay element for the three systems indicated by FIGS. 2, 3, and 4.

TABLE I

Figure 1:
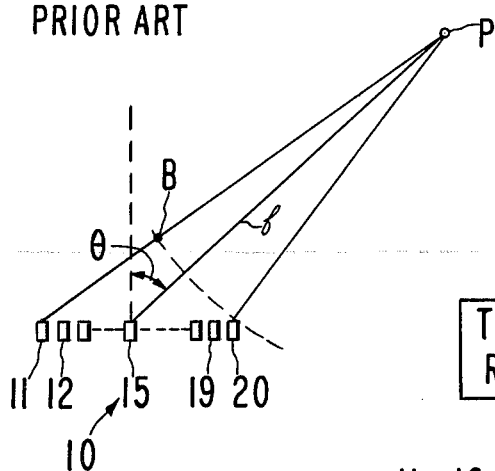
FIG. 1 is a prior art sketch illustrating the impingement of an ultrasonic wave front upon an array of transducers in an ultrasonic imaging apparatus.
Figure 2:
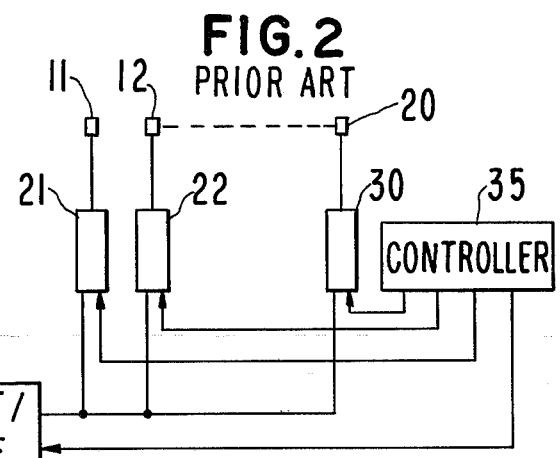
FIG. 2 illustrates in block-diagram form one particular ultrasonic imaging apparatus known to the prior art.

| System | | |
|---|---|---|
| FIG. 2 | 46 | 227 |
| FIG. 3 | 3 | 8 |
| FIG. 4 | 2 | 4 |

The second column gives the number of elements required by the formulas given above where a phase accuracy of $\pm \lambda/8$ is required. In some systems it may be desirable to have higher phase accuracy and the third column of Table I indicates the number of delay steps $n$ for each variable delay element when an accuracy of $2/20 \Delta/20$ is required. In making these calculations it has been assumed that the array has a total of N = 32 elements and that each element is spaced from its adjacent element by A typical operating frequency might be 2.5 MHz. In this case the minimum step values for $\pm \lambda/8$ phase error would be 100 nanoseconds and for $\pm \lambda/20$ phase error 40 nanoseconds.

The maximum delay $Y_{max}$ required of an adjustable delay element 51, 52, . . . 60 is given by d/c sin max. With a spacing between transducer elements $d = \lambda/2$ an operating frequency of 2.5 MHz, and a maximum scan $\theta$ max = 45°, Y max = 141 nanoseconds.

FIG. 5 is a schematic diagram illustrating one embodiment of the present invention. In this system, amplifiers are used in combination with the delay element to compensate for signal amplitude losses that occur within the delay elements and to provide optimum impedance matching; thereby eliminating undesired reflections or reverberations within the delay elements. In this system, transducer elements 11, 12, . . . are coupled through a transmit-receive circuits 92 to the transmitters 93 and receiver preamplifiers 94. The timing signals for the transmitters are derived from the transmitter controller 36 which in turn is controlled by the master programmer 37. The receiver preamplifiers 94 may also be used to provide gain compensation so that echoes from distant objects are amplified to a greater extent than echoes from nearby objects. This is readily achieved by a circuit that increases the gain of these amplifiers after the transmit pulse has taken place by providing a predetermined gain characteristic as a function of time. The timing signals for these gain changes may be provided by master programmer 37. The preamplifiers 94 may also contain circuits to logarithmically compress the incoming signals to further compensate for the differences of signal strengths from nearby objects as compared to more distant objects. The outputs of the preamplifiers 94 are coupled through resistors 95 to the summing junction 96 of inverting amplifier 97. The output of inverting amplifier 97 is coupled through matching resistor 98 to the respective delay lines 51, 52 . . . 60. The gain of these amplifier systems are nominally set to unity through selection of feedback resistor 99. The output impedance of delay line 51, 52 . . . is matched by means of resistor 101 to the desired characteristic impedance. Any gain losses in delay lines 51, 52 . . . 60 can be compensated by feedback resistor 102 of the inverting output amplifier 103. The output resistor 104 serves as an input summing resistor when, for example, switch 60 is closed to couple the delayed output of transducer 11 to the signal from transducer 12. The switching operation in the receive mode is identical to that described above in FIG. 4. The output signal from the receiver 105 is coupled to display 106 where it modulates the brightness of its cathode-ray display tube 107. Master programmer 37 controls the X-Y position of the cathode-ray beam to provide a scan line that has its orientation related to the direction of the received ultrasonic beam as determined by the delay line switching combination selected by receiver controller 38.

The preamplifiers 94 provide amplification of the signals from transducer elements 11, 12-20 to achieve a signal level above the noise level of the delay lines and switches and thereby improve the sensitivity of the system. Preamplifiers 94 also provide unidirectional amplification thereby preventing signals in the delay line circuits from reradiating signals through the transducer elements 11, 12 . . . 20.

Steering angle information contained in master controller 37 is fed to the transmitter controller 36, which generates timing signals for the transmitters 93 coupled to each transducer 11, 12, . . . 20. These timing signals cause each transmitter 93 to produce an electrical pulse in proper timed relationship to cause the corresponding ultrasonic energy pulses emitted by transducer elements 11, 12 . . . 20 to add in phase in the direction and focal depth selected by the master programmer 37. Any acoustical impedance discontinuities will cause a part of the ultrasonic energy to be reflected back toward the transducer elements.

The reflected ultrasonic energy is converted to electrical signals by means of transducer elements 11, 12, . . . 20 and coupled through the transmit-receive coupling network 92 to preamplifiers 94. The outputs of the preamplifiers are coupled to the delay line network and switches as described above wherein signals arriving from the selected direction and focal depth are added coherently and fed into receiver 105. In receiver 105 the signals are further amplified and rectified by a radio-frequency detector circuit. The detected signals may be further amplified in a video amplifier contained in receiver 105 and further processed, for example, by a logrithmic amplifier to produce an output signal that is coupled to display 106. The output voltage is thus a measure of the reflected signal amplitude from the selected direction and depth and the time of the occurrance of this signal is directly related to the depth from which the reflection takes place. Thus by applying this output signal to the display 106 so that it modulates the intensity of the cathode-ray tube 107, a bright spot is formed such that the brightness is related to the scattering cross section of the object producing the reflected signal. The master controller applies proper voltages to the X and Y axes of the cathode-ray tube so that a straight line is drawn that has an orientation related to the direction of the received signal. The time delay of the output signal from receiver 105 after the transmitter pulse determines the range of the object and by sweeping the radial lines of the display at the proper predetermined rate, the distance of the bright spot from the apex gives a direct measure of the range of the scattering object.

In a typical system, the display might consist of 64 radial lines, that is the master controller will program the transmitter controller and receiver controller to sequentially select 64 different steering angles. For one particular angle the transmitters will all fire within a period of about 6 microseconds. Following that, the receivers will be sensitive to incoming signals for about 200 $\mu$ secs. Since the velocity of sound in the human body is approximately 1.5 millimeters/$\mu$sec and the signal must travel to the point of reflection and back to the transducers, a total range available for display is approximately 26 cm. Following this period, there is another period of perhaps 300 $\mu$ secs that can be used to allow any residual signals or reverberations to die down and simultaneously for the master controller to feed new information to the transmitter and receiver controllers and for the receiver controller to select the delay values and switch positions for the next radial scan line. With a total of 64 scan lines, one obtains a complete picture at a rate of approximately 30 frames/sec thereby permitting a real time display of moving objects such as the heart.

The above description of the preferred embodiment of the present invention has been described with specificities which should not be construed as limitations upon the scope of the invention. The scope of the invention is to be construed according to the following claims and their legal equivalents.

What is claimed is:

1. An ultrasonic imaging system comprising first and second electromechanical transducer elements, first and second electronic variable delay elements, each delay element having an input terminal and an output terminal, said first transducer element being connected to said input terminal of said first delay element and said second transducer element being connected to said input terminal of said second delay element, and switching means for selectively providing electrical connection between either said output terminal of said second delay element and said input terminal of said first delay element, or said output terminal of said first delay element and said input terminal of said second delay element, or said output terminal of said second delay element and said output terminal of said first delay element.

2. The ultrasonic imaging system of claim 1, wherein said first and second transducer elements are disposed adjacent each other in an array of transducer elements.

3. The ultrasonic imaging system of claim 2 wherein said array of transducer elements is linear.

4. The ultrasonic imaging system of claim 2 wherein the transducer elements of said array are capable of transmitting ultrasonic wave pulses in a predetermined direction.

5. The ultrasonic imaging system of claim 4 wherein during the quiescent period between said transmitted pulses, the transducer elements of said array are capable of generating electrical signals in response to a reflected ultrasonic wave incident thereon from said predetermined direction.

6. The ultrasonic imaging system of claim 5 wherein said variable delay elements cause said electrical signals generated in response to said reflected wave from said predetermined direction to be integrated in a coherent summation.

7. The ultrasonic imaging system of claim 6 wherein said coherent summation signals are displayed on a CRT cathode-ray tube.

* * * * *